United States Patent
Holmqvist et al.

(10) Patent No.: US 11,376,369 B2
(45) Date of Patent: Jul. 5, 2022

(54) SYRINGE

(71) Applicant: Galderma Holding SA, La Tour-de-Peilz (CH)

(72) Inventors: Anders Holmqvist, Värmdö (SE); Max Blomqvist, Uppsala (SE); Jonas Törnsten, Uppsala (SE)

(73) Assignee: Galderma Holdings SA, Zug (CH)

( * ) Notice: Subject to any disclaimer, the term of this patent is extended or adjusted under 35 U.S.C. 154(b) by 282 days.

(21) Appl. No.: 16/066,900

(22) PCT Filed: Dec. 21, 2016

(86) PCT No.: PCT/EP2016/082077
§ 371 (c)(1),
(2) Date: Jun. 28, 2018

(87) PCT Pub. No.: WO2017/114709
PCT Pub. Date: Jul. 6, 2017

(65) Prior Publication Data
US 2019/0001068 A1    Jan. 3, 2019

(30) Foreign Application Priority Data

Dec. 29, 2015  (EP) .................................... 15202927

(51) Int. Cl.
*A61M 5/315* (2006.01)
*A61M 5/178* (2006.01)

(52) U.S. Cl.
CPC ...... *A61M 5/31568* (2013.01); *A61M 5/3158* (2013.01); *A61M 5/178* (2013.01); *A61M 2205/581* (2013.01); *A61M 2205/582* (2013.01)

(58) Field of Classification Search
CPC .......... A61M 5/31535; A61M 5/31568; A61M 5/3158; A61M 5/31566; A61M 2205/581;
(Continued)

(56) References Cited

U.S. PATENT DOCUMENTS

| 5,279,585 A | 1/1994 | Balkwill |
| 5,725,508 A | 3/1998 | Chanoch et al. |

(Continued)

FOREIGN PATENT DOCUMENTS

| EP | 0 554 995 A1 | 8/1993 |
| EP | 0 688 571 A1 | 12/1995 |

(Continued)

OTHER PUBLICATIONS

International Search Report (PCT/ISA/210) dated Apr. 12, 2017, by the European Patent Office as the International Searching Authority for International Application No. PCT/EP2016/082077.
(Continued)

*Primary Examiner* — Jason E Flick
*Assistant Examiner* — Anna E Goldberg-Richmeier
(74) *Attorney, Agent, or Firm* — Foley & Lardner LLP; Sunit Talapatra

(57) ABSTRACT

A syringe including a barrel, a plunger moveably arranged within said barrel, and a plunger rod for driving said plunger. A first engagement member is arranged at the plunger rod, such that a longitudinal movement of the plunger rod yields a rotational movement of said first engagement member. The first engagement member includes a grooved surface. A second engagement member is arranged at the barrel to engage with said grooved surface of the first engagement member, wherein the first engagement member is arranged to move relative to the second engagement member, such that feedback is given to a user as the plunger rod is moved relative to the barrel for driving said plunger. The first engagement member is arranged at said plunger rod with a predetermined play there between.

16 Claims, 3 Drawing Sheets

(58) Field of Classification Search
CPC .......... A61M 2205/582; A61M 5/3156; A61M 5/31576

See application file for complete search history.

(56) References Cited

U.S. PATENT DOCUMENTS

| | | | |
|---|---|---|---|
| 2010/0094206 A1 | 4/2010 | Boyd et al. | |
| 2012/0010575 A1* | 1/2012 | Jones | A61M 5/31551 604/218 |
| 2012/0265151 A1 | 10/2012 | Nzike et al. | |
| 2012/0289908 A1 | 11/2012 | Kouyoumjian et al. | |
| 2013/0197449 A1 | 8/2013 | Franklin | |
| 2015/0238699 A1 | 8/2015 | Butler et al. | |
| 2015/0250950 A1 | 9/2015 | Moser et al. | |
| 2016/0038682 A1 | 2/2016 | Tornsten et al. | |
| 2016/0151574 A1* | 6/2016 | Oakley | A61M 5/3157 604/207 |
| 2016/0271332 A1* | 9/2016 | Bilton | A61M 5/31551 |

FOREIGN PATENT DOCUMENTS

| | | |
|---|---|---|
| EP | 1 923 083 A1 | 5/2008 |
| EP | 2 783 720 A1 | 10/2014 |
| WO | 2006079481 A1 | 8/2006 |
| WO | WO 2008/057976 A2 | 5/2008 |
| WO | WO 2011/039236 A1 | 4/2011 |
| WO | WO 2014/040929 A1 | 3/2014 |
| WO | WO 2014/056635 A1 | 4/2014 |
| WO | 2014153572 A1 | 9/2014 |
| WO | WO 2015/032778 A1 | 3/2015 |

OTHER PUBLICATIONS

Written Opinion (PCT/ISA/237) dated Apr. 12, 2017, by the European Patent Office as the International Searching Authority for International Application No. PCT/EP2016/082077.

International Preliminary Report on Patentability (PCT/IPEA/409) dated Apr. 16, 2018, by the European Patent Office as the International Searching Authority for International Application No. PCT/EP2016/082077.

International Search Report (PCT/ISA/210) dated Apr. 26, 2017, by the European Patent Office as the International Searching Authority for International Application No. PCT/EP2016/082074.

Written Opinion (PCT/ISA/237) dated Apr. 26, 2017, by the European Patent Office as the International Searching Authority for International Application No. PCT/EP2016/082074.

International Preliminary Report on Patentability (PCT/IPEA/409) dated Apr. 16, 2018, by the European Patent Office as the International Searching Authority for International Application No. PCT/EP2016/082074.

International Preliminary Report on Patentability (Form PCT/IPEA/409) dated May 3, 2018, by the Patent Corporation Treaty in corresponding International Application No. PCT/EP2016/082074 (15 pages).

* cited by examiner

SYRINGE

TECHNICAL FIELD

The present invention generally relates to syringes, and more particularly to a syringe that is able to provide a user with feedback during use.

TECHNICAL BACKGROUND

When a user of a medical syringe administers a substance, it is common, in particular within certain areas of treatment, to distribute the total volume carried by the syringe over an area. Some examples of such areas of treatment are dermatology, plastic surgery, cosmetic surgery, and odontology. The distribution is for instance done by inserting the needle of the syringe just beneath and approximately in parallel with the skin surface and then administering the substance while withdrawing the needle. Another way is to administer the substance at several anatomic locations within a limited area, i.e. to administer a fraction of the total volume at each location.

In these, and other, methods of distributing the substance it is an advantage if the syringe is provided with some kind of dosing aid, which aids the user in knowing how large fraction of the total volume of the substance is administered at each location or per time unit.

One known example of dosing aids is the dosing scale traditionally provided on syringes, where known problems include difficulties for a user to see the scale during injection as well as the distraction of attention arising when the user simultaneously tries to read the scale and perform the injection.

Also known are mechanical and electronic injectors. These devices however tend to be more expensive and heavier than traditional syringes. Further problems include the fact that most injectors do not allow aspiration prior to injection, which possesses a considerable drawback for many users.

In order to alleviate some of these drawbacks, attempts have been made to provide a syringe with user friendly means that informs and provides feedback to a user about the injected amount or an injection rate. For example, an effort to provide a syringe with a dosing aid is disclosed in WO2008057976 where an engagement member is provided on the finger grip and engages with a structure of the plunger rod.

However, tests have proven that a first dose with such prior art constructions can be up to three time larger than actually intended and such overdosing can in certain situations be catastrophic for patients causing e.g. unintended muscle paralysis which in turn may cause problems with respect to swallowing, speaking, or breathing, drooping eyelids, lopsided smile, muscle weakness and/or muscle stiffness. Further, problems related to the syringe not providing distinct feedback during certain conditions, such as when the plunger rod is moved at a slow speed with respect to the barrel are also known from the prior art.

SUMMARY OF THE INVENTION

Accordingly, it would be desirable to provide an improved syringe providing feedback to a user during injection about for example the amount delivered. In particular, it would be desirable to provide a more distinct feedback while at the same time increasing the accuracy of the delivered dosage. To better address one or more of these concerns a syringe as defined in the independent claim is provided. Preferred embodiments are defined in the dependent claims.

According to a first aspect of the invention a syringe comprising a barrel, a plunger moveably arranged within said barrel and a plunger rod for driving said plunger is provided. A first engagement member is arranged at the plunger rod, said first engagement member comprising a grooved surface. The arrangement is such that a longitudinal movement of the plunger rod yields a rotational movement of the first engagement member. A second engagement member is arranged at the barrel to engage with said grooved surface of the first engagement member, wherein the first engagement member is arranged to move relative to the second engagement member such that feedback is given to a user as the plunger rod is moved relative to the barrel for driving said plunger. The first engagement member is arranged at said plunger rod with a predetermined play there between.

According to the first aspect, the syringe provides an inventive solution to the concerns described above derived from the realization that the desired functionality may be provided by a design incorporating a first and second engagement member, arranged such that a feedback is provided to the user as the plunger rod is moved relative the barrel, wherein the first engagement member is arranged at the plunger rod with a predetermined play there between. Hereby, i.e. by designing the device such that a play prevails, or exists, between the first engagement member and the plunger rod, the syringe will provide a distinct feedback while at the same time the accuracy of the delivered dose of a substance is increased. Accordingly, advantages of the invention include that the dosage accuracy is significantly improved while, at the same time, the feedback to the user is made more distinct.

Due to the rotational movement of the first engagement member, when the plunger rod travels with respect to the barrel the first engagement member rotates and the second engagement member may engage the rotating grooves (and ridges). In some embodiments, the plunger rod and the first engagement may be described as together forming a linear actuator. A design wherein a rotational movement of the engagement member is induced is an advantageously space efficient design.

The disclosed syringe is suitable for example for applications wherein the syringe is supplied empty. During use, the substance to be injected is first drawn up in to the barrel of the syringe for example from a vial. Examples of such substances include botulinum toxin. In certain application, the substance is then administered to the patient in multiple steps and/or at different injection locations. Due to the design of the syringe, and more particularly the design of the first and second engagement members, a feedback is repeated when the substance is injected, each feedback indication normally corresponds to a certain dose of the substance. The syringe may in some embodiments be a disposable syringe. Suitable materials for the comprised components include plastics; suitable manufacturing methods include injection moulding. The barrel of the syringe is adapted to contain the substance to be administered. The plunger is movably arranged within said barrel and a plunger rod is provided to drive said plunger, in order to for example expel the substance contained in the barrel to be administered through for example a cannula attached to the barrel or in some cases draw the substance into the syringe.

The first engagement member is arranged on the plunger rod and comprises a grooved surface, i.e. a surface comprises ribs, i.e. grooves and/or ridges. The number of grooves, or ridges as well as the distance between the adjacent grooves may be adapted depending on the application.

The second engagement member is adapted to engage with the grooved surface of the first engagement member in order to provide feedback to the user as the plunger rod, on which the first engagement member is arranged, is moved with respect to the barrel. Accordingly, the second engagement member may in some embodiments be arranged at, or connected to, the barrel. One possible form of feedback that may in some embodiments be provided by the second engagement member, and/or by the second engagement member interacting or engaging with the first engagement member is an audible feedback, i.e. a sound such as a click-sound. Other examples include tactile feedback. In some embodiments, each feedback indication may correspond to the second engagement member travelling over one groove of the first engagement member.

In order to achieve a reliable, distinct feedback indication regardless of for example the travelling speed of the plunger rod, the invention according to the independent claims comprise a design wherein the first engagement is arranged at the plunger rod with a play there between. Accordingly, in some embodiments, a gap may be prevailing in the arrangement, or engagement, between the plunger rod and the first engagement member such that the first engagement member although in a sense travelling, or moving, with the plunger rod, is further allowed to move a short predetermined distance with respect to the plunger rod. In that the relative movement of the first engagement member is allowed, i.e. due to the play between the first engagement member and the plunger rod, a free acceleration of the first engagement member is allowed. In some embodiments, the first engagement member travels in a direction coinciding with a direction of movement of the plunger rod. In some embodiments, the first engagement member travels in a direction different from a direction of movement of the plunger rod.

The implications of this functionality of the claimed invention may be better understood when described in combination with the functionality of the engagement between the first and the second engagement member. The first engagement member is arranged on the plunger rod and moves as the plunger rod moves relative the barrel. The first engagement member further comprises grooves with which the second engagement member engages as the plunger rod moves with respect to the barrel. In one embodiment, in what may be described as a first (or initial) stage of engagement, the second engagement member engages for example a first groove of the grooved surface of the first engagement member. As the plunger rod and consequently the first engagement member moves, the second engagement member moves along for example an adjacent ridge in order to engage for example a second adjacent groove of the first engagement member, i.e. into what may be described as a second stage of engagement. Due to the arrangement of the first engagement member on the plunger rod, more particularly the play there between, the first engagement member is kept in engagement by the second engagement member while the plunger rod may travel a certain predetermined distance, i.e. a relative movement is allowed due to the play between the plunger rod and the first engagement member. However, after a predetermined relative movement corresponding to the play between said plunger rod and the first engagement member, the first engagement member moves again with the plunger rod and the engagement between the first and second engagement member is released. Hereby, due to the play prevailing between the first engagement member and the plunger rod, the first engagement member is allowed to accelerate freely until stopped dead by an engagement of the second engagement member with for example the next groove. This stop, i.e. engagement, produces a feedback to the user. This feedback may in some embodiments be an audible sound, i.e. a "click-sound".

Accordingly, the engagement between the first and the second engagement member may in some embodiments be described as an engagement adapted to stop a movement of the first engagement member. In some embodiments, the act of stopping the movement of the first engagement member may produce a feedback, for example an audible sound. Due to the play, i.e. the allowed free relative movement, and hence the free acceleration of the first engagement member, a reliable mechanism for producing a feedback is ensured. This since problems in the known art related to lack of sufficient acceleration of comprised parts for example when the plunger rod is moved slowly and one engagement member slowly slides along the other thereby not producing a distinct feedback, have been addressed.

A further advantage of the disclosed syringe is that due to the design of the present first engagement member, known problems relating to the accuracy of dosage, in particular the accuracy of the first dose administered after the substance has been drawn into the syringe from a vial or the like, are reduced. This is at least partly due to the design wherein the plunger rod may for example in some embodiments be allowed to move in both directions, while the feedback to the user is generated irrespective of the travelling direction of the plunger rod. This is of particular importance for the first dose after filling the syringe, i.e. the first feedback indication. Prior to the delivery of the first dose, the direction of movement of the plunger rod is reversed. Due to the design of the arrangement of the first engagement member and the plunger rod and the functionality of the engagement of the first and second engagement members as described in the preceding paragraphs, the design easily lends itself to what may in some embodiments be described as a symmetric layout wherein the behaviour of the comprised components is the same regardless of the direction of movement of the plunger rod. In order to achieve the high dosage accuracy, the size of the play between the first engagement member and the plunger rod, what in some embodiments may be referred to as a gap, must be chosen large enough to generate a distinct feedback, for example an audible sound, but otherwise as small as possible.

According to one embodiment, the play between the first engagement member and the plunger rod prevails independent of the direction of movement of the plunger rod, according to one embodiment, the predetermined relative motion between the first engagement member and the plunger rod is allowed independent of the direction of movement of the plunger rod. According to one embodiment, the play between said first engagement member and said plunger rod comprises substantially the same magnitude in a first direction of movement and in a second direction of movement.

Further, due to the free acceleration of the first engagement member being allowed, not only is a distinct feedback provided to a user but a situation such as what is known from the prior art wherein the first engagement member may stop to an undesired rest at an intermediate position between ridges when the plunger rod moves slowly, thereby allowing a too large dose to be administered when travelling along to provide a next feedback to the user is highly unlikely to occur in the present invention.

According to one embodiment, the play allows for a relative movement between the first engagement member and the plunger rod wherein the first engagement member and the plunger rod move independently of one another. For example, the relative movement allowed may be described as a free movement. In one embodiment, the relative movement may be understood as a movement wherein the first engagement member and the plunger rod move independently of one another, in contrast to the cooperating, or interacting, movement of the plunger rod and the first engagement member yielded by an engagement between the plunger rod and the first engagement member. In one embodiment, the predetermined relative movement is a movement wherein the first engagement member may accelerate freely over a predetermined distance with respect to the plunger rod.

In one embodiment, the grooves of the grooved surfaces are adapted to extend in a direction parallel to the longitudinal axis of the plunger rod. In one embodiment, the grooves of the grooved surface of the first engagement member are adapted to extend in a direction such that a tangent to one of the grooves is perpendicular to the longitudinal axis of the plunger rod.

According to one embodiment, the syringe further comprises a guiding element adapted to restrain a rotational movement of said plunger rod. Hereby, the rotation of the plunger rod may be constrained and the click wheel may be rotated as the plunger rod is moved longitudinally, i.e. in and out of the barrel.

According to one embodiment, the guiding element comprises a hole adapted to receive the plunger rod, the hole comprising means for constraining a rotation of said plunger rod. In one embodiment, said means comprise a first and second flat surface of the hole through which the plunger may be received. In one embodiment, the plunger rod comprises a first and a second substantially flat surface adapted to engage said first and second corresponding flat surface of the hole, such that a rotation is constrained.

According to one embodiment, the second engagement member further comprises a guiding element adapted to restrain a rotational movement of said plunger rod. Hereby, the rotation of the plunger rod may be constrained and the click wheel may be rotated as the plunger rod is moved longitudinally, i.e. in and out of the barrel. According to one embodiment, the guiding element adapted to restrain a rotational movement of said plunger rod is formed as an integral component with said second engagement member. Hereby, the rotation of the plunger rod may be constrained and the click wheel may be rotated as the plunger rod is moved longitudinally, i.e. in and out of the barrel.

According to one embodiment, the predetermined relative movement between the plunger rod and the first engagement element is at least a relative rotation. According to one embodiment said predetermined play is at least a predetermined rotational play. Accordingly, in such an embodiment, the first engagement element may be allowed to rotate a predetermined distance, e.g. a predetermined angle, relative to the plunger rod. In one embodiment, the predetermined relative movement, and/or the play, is a relative movement or play along the longitudinal axis of the plunger rod. In other embodiment, the predetermined relative movement, and/or play, is a combined rotational and longitudinal relative movement and/or play.

According to one embodiment, the plunger rod comprises at least one of a helical groove and a helical protrusion. The pitch of the helical groove/protrusion may be chosen to fit different applications. A lower pitch may be preferable in order to lower the resisting force when the plunger rod is pushed by the user. In one embodiment, the at least one helical groove or protrusion may be referred to as a thread, or threading, of the plunger rod.

According to one embodiment, the first engagement member comprises means for engaging the at least one of a helical groove and a helical protrusion. In one embodiment, said means are a corresponding helical groove or protrusion. In some embodiments, such a helical groove or protrusion may be referred to as a thread, or threading, of the first engagement member.

Accordingly, the first engagement member may be arranged on the plunger rod by means of a thread fitting.

According to one embodiment, the predetermined relative movement between the first engagement member and the plunger rod is allowed by means of a gap in the engagement between said first engagement member and said plunger rod. Accordingly, a predetermined relative movement is allowed corresponding to the size of the gap of the engagement. In one embodiment, the gap is such that the predetermined relative movement is substantially of the same magnitude irrespective of the direction of movement of the plunger. In one embodiment, the gap may be a gap in the thread fitting between the first engagement member and the plunger rod.

According to one embodiment, the second engagement member is made from metal, for example sheet metal. In other embodiment, the second engagement member may be casted o moulded and/or comprise a plastic material.

According to one embodiment, the second engagement member comprises an engaging member adapted to engage the grooved surface of the first engagement member, wherein the engaging member is movable between a first stage, wherein the engaging member engages with a groove and a second stage wherein the engaging member engages a protrusion. Such a protrusion is a protrusion between adjacent grooves, i.e. a protruding structure separating two grooves which may also be referred to as a rib.

According to one embodiment, the second engagement element is adapted to move in a plane generally perpendicular to a longitudinal direction of said plunger rod as the plunger rod is moved relative to the barrel. According to one embodiment, the engaging member is adapted to move in a plane generally perpendicular to a longitudinal direction of said plunger rod as the plunger rod is moved relative to the barrel. Examples of such an engaging member may be an engaging member comprising a flexible arm adapted to move in said plane. According to one embodiment, the engaging member moves in a radial direction of the barrel.

According to one embodiment, the engaging member is tensioned at least in the second stage. In one embodiment, the engaging member is a pre-tensioned, or biased, elastic element. Examples include a spring element made of plastic; a spring element made of metal such as for example feather steel, or a metal or plastic tongue. The tensioning of the engaging member further contributes to the improvement of the feedback produced, i.e. the click-sound.

According to one embodiment, the engaging member comprises a protruding element adapted to engage said grooved surface. Such a protruding element improves the engagement between the first and second engagement element. Examples include a hatch, a ratchet or a hook. In one embodiment, the protruding element is arranged to protrude from an elastic member of the engaging element.

According to one embodiment, the second engaging element comprises at least two engaging members adapted to engage the grooved surface of the first engagement member, wherein the at least two engaging members are movable between a first stage, wherein the engaging members respectively engage with a groove and a second stage wherein the engaging member respectively engage a protrusion.

According to one embodiment, the at least two engaging members are arranged on opposite sides of the second engagement element. According to one embodiment, the at least two engaging members are angularly offset approximately 180°.

According to one embodiment, the second engagement member is adapted to at least partly surround said plunger rod. Such an embodiment facilitates a space efficient design of the syringe. In one embodiment, the second engagement member is a cylindrical element surrounding said plunger rod.

In one embodiment, the second engagement member is arranged at the barrel. In one embodiment, the second engagement member is adapted to at least partly surround the barrel. According to one embodiment, the second engagement member is arranged adjacent to an end of the barrel. According to one embodiment, the second engagement member is arranged within the barrel.

According to one embodiment, the second engagement member comprises a main part comprising a substantially circular or semi-circular cross section and a movable structure adapted to engage said grooved surface of the first engagement member. In one embodiment, the main part of the second engagement member is cylindrical, comprising a cut out to allowing for a movement of the movable structure. This is another example of a space efficient design.

According to one embodiment, the movable structure adapted to engage said grooved surface of the first engagement member has a curved shape. Examples include circular arc shapes of different lengths and radii.

According to one embodiment, the second engagement member comprises an elastic element adapted to engage the grooved surface of the first engagement member. Such an elastic element may be movably arranged. Examples include a spring element made of plastic, a spring element, or spring member, made of metal such as for example feather steel, a steel wire element or a metal or plastic tongue. In one embodiment, the elastic element is a pre-tensioned, or biased, elastic element. According to one embodiment, the second engagement member comprises a protruding element adapted to engage said grooved surface. Such an element improved the engagement between the first and second engagement element. Examples include a hatch, or a hook. In one embodiment, the protruding element is arranged to protrude from an elastic member of the second engagement element.

According to one embodiment, the first engagement member is a wheel, or comprises a wheel shape. Such a first engagement member is space efficient and especially suitable for a case wherein the relative rotational movement between the first engagement member and the plunger rod is at least partly rotational. The wheel may comprise the surface comprising grooves, or ridges and may be referred to as a click-wheel.

According to one embodiment, the number of grooves of the grooved surface of the first engagement element lies in the range of 1-15, preferably in the range of 5-10.

Further, according to one embodiment, the distance travelled by the plunger rod corresponding to the second engagement moving between two adjacent grooves (or ridges) of the first engagement element, i.e. a dose, lies in the interval of 0-5 mm, preferably in the interval of 0.5-2 mm. According to one embodiment, the volume of (the barrel) of the syringe lies in the interval of 0-5 ml, preferably in the interval of 0.25-0.75 ml. According to one embodiment, the inner diameter of (the barrel) of the syringe lies in the interval of 0-5 mm, preferably in the interval of 2-4 mm.

Further objectives of, features of and advantages with the present invention will become apparent when studying the following detailed disclosure, the drawings and the appended claims. Those skilled in the art realize that different features of the present invention can be combined to create embodiments other than those described in the following.

BRIEF DESCRIPTION OF THE DRAWINGS

The invention will be better understood through the following illustrative and non-limiting detailed description of preferred embodiments, with reference to the appended drawing, on which.

All figures are schematic, not necessarily to scale, and generally only show parts which are necessary in order to elucidate the invention, wherein other parts may be omitted or merely suggested.

DETAILED DESCRIPTION OF EMBODIMENTS

Figure 1:
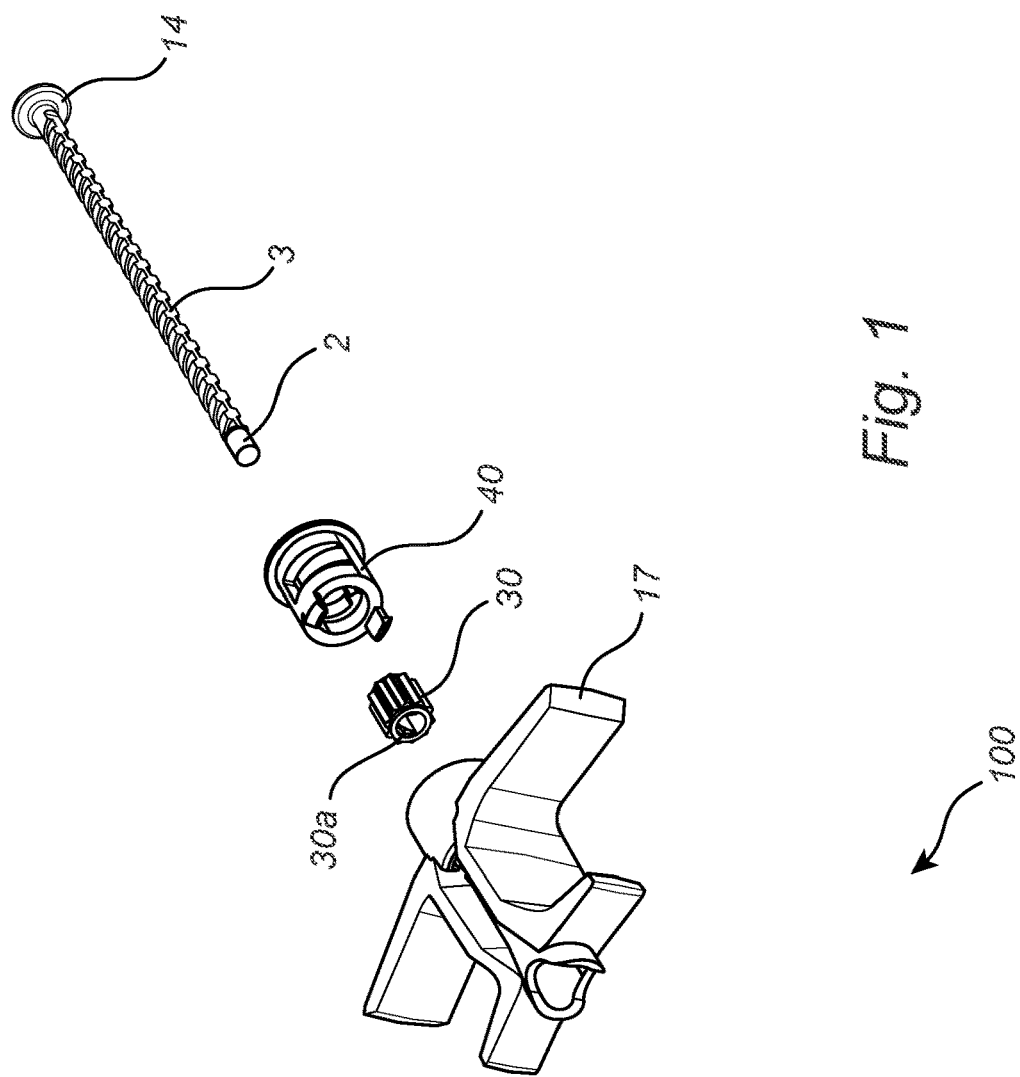
FIG. 1 is an exploded perspective view of a syringe according to one embodiment of the invention.
Figure 1:
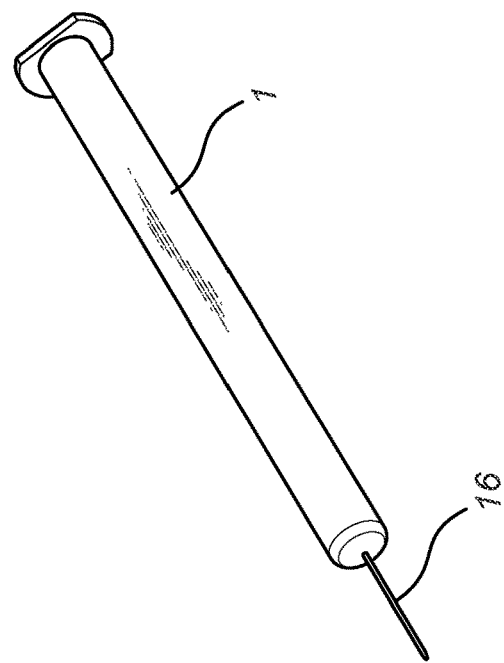

A syringe 100 according to an embodiment of the invention is shown in FIG. 1. The syringe comprises a barrel 1, a plunger 2 moveably arranged within the barrel 1 and a plunger rod 3 for driving the plunger 2. The plunger rod is further provided with a thumb plate 14 for activation of the plunger rod 3. The plunger rod 3 is adapted to drive the plunger 2, i.e. to engage the plunger 2 such that the plunger 2 may preferably be moved in both directions though the barrel. Suitable engagement means may be provided to allow for this engagement. The syringe 100 further comprises a needle 16. The barrel may be provided with a finger grip 17.

Figure 2:
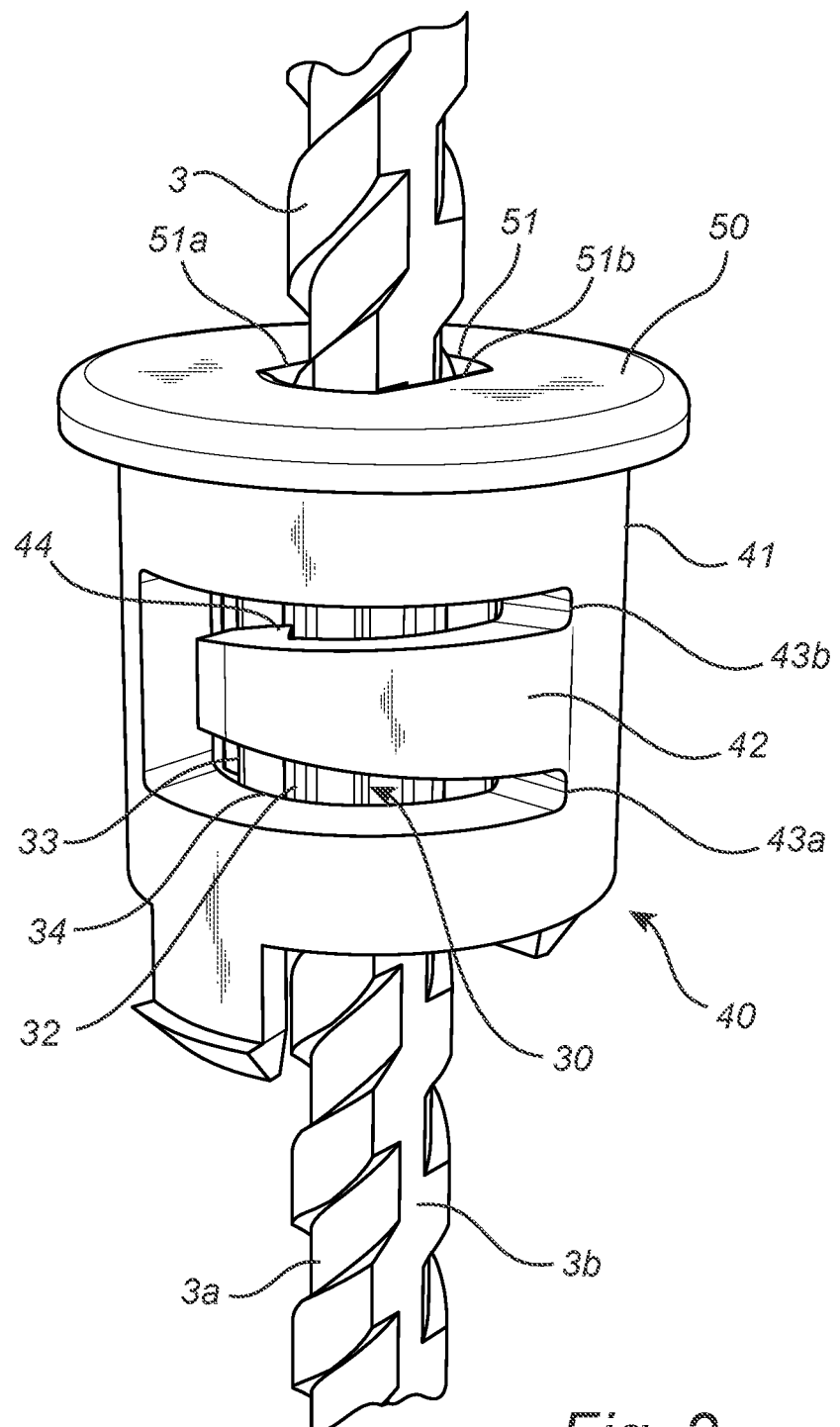
FIGS. 2 and 3 are detailed perspective views of some of the comprised components of a syringe according to an embodiment of the invention.

The syringe further comprises a first engagement member 30 arranged at the plunger rod 3, shown in FIG. 2. The first engagement member 30 has a substantially circular, or annular shape, i.e. may be described as having a wheel shape. Further, the first engagement member 30 comprises a grooved surface 32 comprising a plurality of ribs, i.e. alternating ridges, or protrusions, 33 and grooves, or valleys 34, provided in an alternating manner along the surface 32. The grooved surface 32, and consequently the plurality of grooves and ridges, is/are provided along the circumference of the first engagement member. The ridges (and grooves) typically comprise a symmetrical shape, although many shapes are conceivable, and may for example be provided by providing the first engagement member with a suitable number of grooves defined by flanges. The shape of the flanges may vary depending on the field of use of the syringe. In the illustrated embodiment, the ridges (and grooves) extend in a direction substantially parallel to a longitudinal direction of the plunger rod. The distance between the centre points of adjacent ridges in the embodiment illustrated in FIG. 2 is typically between 0 and 1 mm. The distance is typically adapted to the substance to be injected and the size of the barrel. A small diameter of the barrel implies a small amount of substance being expelled due to a certain travel of the plunger rod, accordingly the distance between ridges may have to be larger for such a case.

A second engagement member 40, shown in FIG. 2, is arranged at an upper end of the barrel 1 to engage with the grooved surface 32 of the first engagement member 30, such that feedback is given to a user as the plunger rod 3 is moved relative to the barrel 1 for driving the plunger 2.

The second engagement member 40 is adapted to engage with the grooved surface 32 of the first engagement member 30 in order to provide feedback to the user as the plunger rod 3, on which the first engagement member 30 is arranged, is moved with respect to the barrel 1. The feedback is generated by interaction between the first engagement member 30 and the second engagement member 40, since the first engagement member 30 is arranged to move relative to the second engagement member 40, as will be further described below. The second engagement member 40 is in the illustrated embodiment arranged at an upper end of the barrel 1. The second engagement member 40 is further arranged at the barrel and comprises a substantially cylindrical main part 41 and a first and a second movable structure, i.e. a first arm 42 and a second arm (not shown) adapted to engage the grooved surface 32 of the first engagement member 30. The first and second arms are arranged on opposite sides of the second engagement member, i.e. angularly offset approximately 180°. The cylindrical main part 41 is arranged surrounding the plunger rod 3 and has a first and second cut out portion 43a, 43b allowing for a movement of the arm 42. The functionality of the first and second arms and related structures such as the cut out 43 will in the following be described with reference to a single arm 42.

The movable arm 42 is adapted to engage the grooved surface 32 of the first engagement member and has a curved shape, i.e. extend circumferentially along the main part and/or the barrel. The exemplary arm is made from a flexible, or resilient, material. Further, the arm may be described as being formed, or shaped, corresponding to the shape of the cut-out of the cylindrical shape. The movable, or flexible, arm 42 is adapted to move in a plane substantially perpendicular to a longitudinal direction of the plunger rod 3 as the plunger rod 3 is moved relative to the barrel 1. Further, the flexible arm 42 comprises a protruding element 44, or a hatch 44, adapted to engage the grooved surface 32, or to improve the engagement. The protruding element 42 is integrally formed, or designed, with the movable arm 42 of the second engagement element 40.

Figure 3:
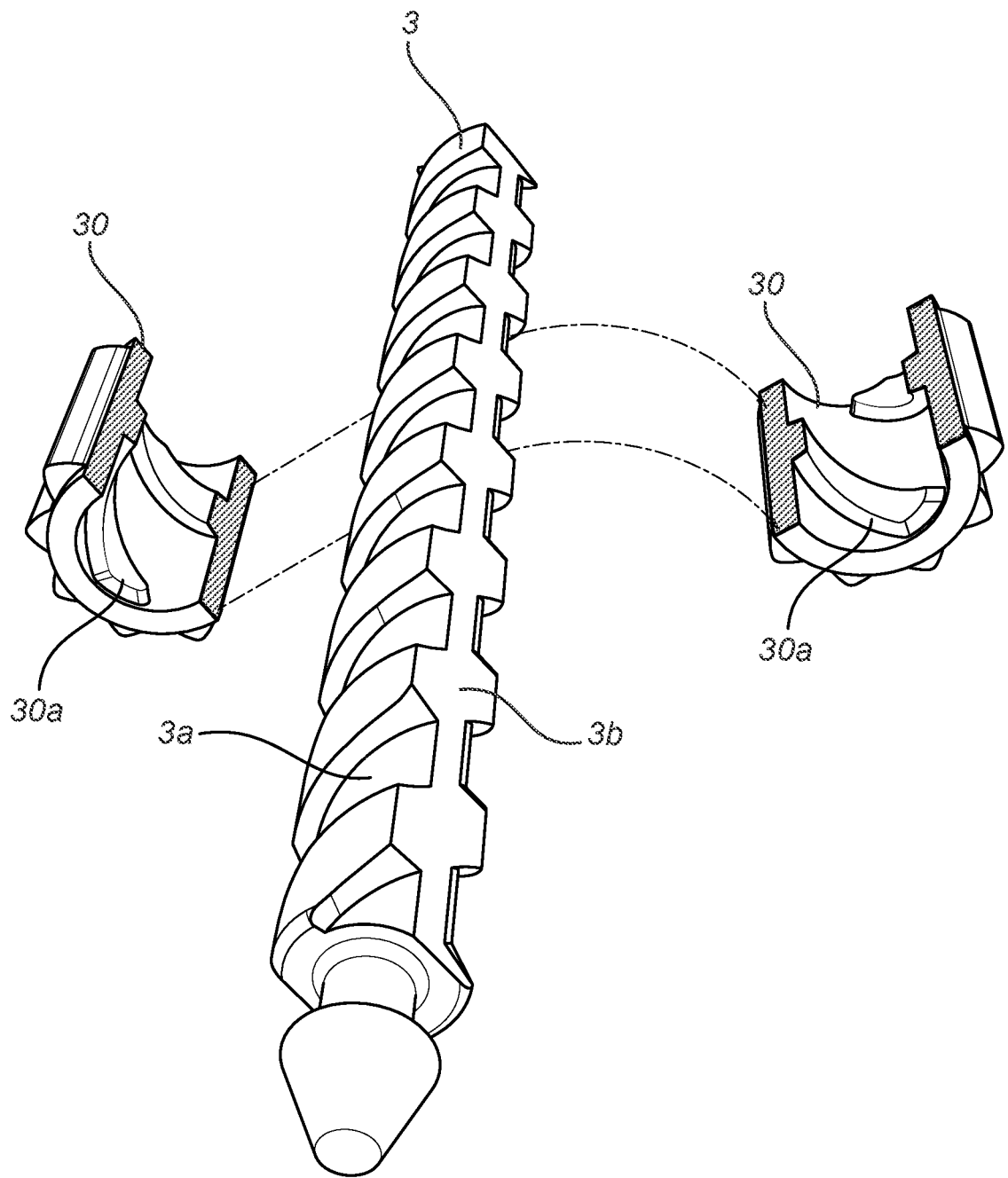

The first engagement member 30 and the plunger rod 3 are adapted to engage such that a longitudinal movement of the plunger rod 3 yields at least a rotational movement of the first engagement member 30. In the illustrated embodiment, the engagement is achieved by means of a thread fitting between the plunger rod 3 and the first engagement member 30. The plunger rod 3 comprises a helical groove 3a, and the first engagement member 30 comprises a corresponding protruding helical structure 30a, i.e. a thread fitting, as best shown in FIG. 3. Further, a guiding element 50 is arranged on the syringe, in the illustrated case the guiding element 50 is arranged at a first end of the second engagement element 40 and further within the cylindrical main part 41 of the second engagement member 40. Accordingly, the guiding element 50 comprises a substantially circular cross section, wherein the diameter corresponds to the inner diameter of the cylindrical main part 41. The guiding element 50 is adapted to restrain a rotation of the plunger rod 3 such that the plunger rod 3 moves in a longitudinal direction while yielding a rotational movement of the first engagement member 30. In order to engage the guiding element 50, the plunger rod 3 comprise a first substantially flat surface 3b and an opposite second substantially flat surface (not shown) adapted to engage a first and a second corresponding flat surface 51a, 51b of a hole 51 in the guiding element 50 through which the plunger rod 3 extends, such that a rotation is constrained.

Further, the thread fitting between the plunger rod 3 and the first engagement member 30 is designed to allow for the play, i.e. the predetermined free relative movement between the plunger rod 3 and the first engagement member 30. Hereby, a gap (play) in the engagement between the first engagement member 30 and the plunger rod 3 is arranged, i.e. a gap (play) in the thread fitting in the illustrated case. In other words, the width of the helical groove 3a of the plunger rod 3 is different from the width of the corresponding engaging structure of the first engagement member 30, i.e. the protruding helical structure 30a, and more particularly the ridges constituting the helical structure 30a, such that a small relative free, or independent, movement between the first engagement member 30 and the plunger rod 3 is allowed, i.e. a play prevails or exists. By relative movement should be understood a movement wherein the first engagement member 30 and the plunger rod 3 move independently of one another, in contrast to the cooperating, or interacting, movement of the plunger rod 3 and the engagement member, or element, 30 yielded by the engagement (i.e. the threading) between the plunger rod and the first engagement element when engaged. Accordingly, the first engagement member 30 may, although in a sense being adapted to travel, or move, with the plunger rod 3, be further allowed to move freely a short predetermined distance with respect to the plunger rod. In that the free movement, or the play, of the first engagement member is allowed, a free acceleration of the first engagement member is allowed. In the illustrated case the predetermined relative movement is a combined relative rotation and relative longitudinal movement, since due to the thread fit between the first engagement member 30 and the plunger rod 3 combined with the guiding element 50 constraining the rotation of the plunger rod 3, the first engagement member 30 rotates and the plunger rod 3 performs a longitudinal movement.

In the embodiment shown in FIG. 1, the feedback that is provided by the movable arm 42 of the second engagement member 40 interacting or engaging with the grooved surface 32 of the first engagement member 30 is an audible feedback, i.e. a sound. Each click corresponds to the movable arm 42 of the second engagement member 40 travelling over one groove (or ridge) of the first engagement member 30. This functionality will be described in conjunction with the functionality of the engagement between the first 30 and the second engagement member 40 in the following.

The first engagement member 30 is arranged on the plunger rod 3 and consequently moves as the plunger rod 3 moves relative the barrel 1, the arm 42 of the second engagement member 40 engages the grooves 32 of the first engagement member 30 as the plunger rod 3 moves with respect to the barrel 1. In what may be described as a first stage of the engagement, the arm 42, and more particularity the protrusion of the arm 44, engages a first groove. This first stage may be described as an initial position wherein the arm 42 is at rest, i.e. in a non-tensioned state. As the plunger rod 3 moves longitudinally with respect to the barrel 1 and the first engagement member 30 consequently rotates, the arm 42 moves outwards in a radial direction when sliding up the next ridge 33 of the grooved surface 32. This corresponds to a tensioned stage of the arm 42. Subsequently, the arm 42 is to engage a second adjacent groove of the first engagement member 30, i.e. move into a stage of engagement in which the arm 42 returns to its initial position. Due to the arrangement of the first engagement member 30 on the plunger rod 3 wherein a play prevails between the plunger rod 3 and the engagement member 30, the first engagement element 30 may be kept in engagement with the arm 42. In such an engagement, the second engagement member 40 constrains the rotation of the first engagement member by means of the arm 42 and the protrusion 44. However, after a predetermined relative movement corresponding to the amount of play between said plunger rod 3 and the first engagement member 30, the engagement between the first and second engagement member is released. At this stage, due to the play (in the illustrated case the exemplary gap in thread fitting), the first engagement member 30 accelerates freely until stopped dead by the second engagement member 40 engaging the next groove, this stop, i.e. engagement, produces an audible sound, i.e. a "click-sound".

Accordingly, the engagement between the first and the second engagement member may be described partly as an engagement adapted to stop a free movement of the first engagement member 30, wherein the act of stopping the free movement of the first engagement member is such that an audible sound is produced. This is due to the allowed free relative movement, and hence the free acceleration of the first engagement member 30. The first engagement member 30 is allowed to accelerate in rotation, at least in part due to the tension in the movable arm 42 only able to move in and out in a radial direction. When the arm reaches a groove between two ribs and is stopped hard by the next rib, a click sound is produced.

The first engagement member 30, in the illustrated case a "click wheel", is allowed to rotate a short distance freely by means of the gap, or play, in thread fitting between the wheel 30 comprising ribs (i.e. the grooves and ridges) and the plunger rod 3. If there is no gap, or slack, in such a thread fitting allowing the clock wheel to accelerate in rotation and an injection occurs slowly there will be no sound generated as the arm 42 of the second engagement member 40 would slide slowly down the rib and then slowly climb up the next rib.

Accordingly, the mechanism allowing for feedback to the user disclosed in the present specification, the size of the first dose achieved after a change of direction of movement may be designed, or adapted, by means of the design of the size, or magnitude, of the allowed relative movement between the plunger rod 3 and the plunger 2. The size of the relative movement, or play, is preferably adapted to be as small as possible still achieving clicks.

Hereby a very minor dose size variation may be achieved for example when the direction of movement of the plunger rod is reversed While the invention has been illustrated and described in detail in the drawings and foregoing description, such illustration and description are to be considered illustrative or exemplary and not restrictive; the invention is not limited to the disclosed embodiments. The skilled person understands that many modifications, variations and alterations are conceivable within the scope as defined in the appended claims.

Additionally, variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope of the claims.

The injection of botulinum toxin has been mentioned as a possible area of use for the device according to the invention. Naturally, it is possible to use the device according to the present invention with other liquid compositions, and gel compositions, such as hydrogels. The device is also useful for injecting cross linked or non-cross linked hyaluronic acid gels and other types of dermal fillers than hyaluronic acid, e.g. collagen, calcium hydroxyl apatite, poly-L-lactic acid (PLLA), other polysaccharides and polymethylmethacrylate (PMMA). Furthermore, the device is useful for injecting liquid compositions comprising active substances and/or bioactive agents, such as local anaesthetics, cicatrizants, antioxidants, insulin or growth hormones. One preferred liquid composition of this type is a gel composition with a hyaluronic acid gel carrier and an active substance and/or a bioactive agent, e.g. a local aesthetic or a cicatrizant, such as dextranomer beads.

The invention claimed is:

1. A syringe, comprising:
   a barrel,
   a plunger moveably arranged within said barrel and a plunger rod for driving said plunger,
   a first engagement member having a substantially circular shape, arranged at the plunger rod such that a longitudinal movement of the plunger rod yields a rotational movement of said first engagement member, said first engagement member comprising a grooved surface; and
   a second engagement member arranged at the barrel, and comprising an engaging member adapted to engage with the grooved surface of the first engagement member, wherein the engaging member is movable between a first stage, wherein the engaging member engages with a groove, and a second stage, wherein the engaging member engages with a protrusion, wherein the first engagement member is arranged to move relative to the second engagement member such that at least one of audible or tactile feedback is given to a user as the plunger rod is moved relative to the barrel for driving said plunger,
   wherein said first engagement member is arranged at said plunger rod with a predetermined play there between provided by a gap in the engagement between the first engagement member and the plunger rod, wherein said play allows for a predetermined relative movement between said first engagement member and said plunger rod, wherein the first engagement member and the plunger rod move independently of one another, and the first engagement member is allowed to accelerate until stopped by an engagement with the engaging member of the second engagement member, and
   wherein the engaging member comprises an arm configured to engage the first engagement member, and the second engagement member comprises a plurality of cut-outs disposed to accommodate movement of the arm, the plurality of cut-outs comprising a first cut-out parallel to a second cut-out extending along opposing surfaces of the arm.

2. The syringe according to claim 1, wherein the predetermined relative movement between said first engagement member and said plunger rod is allowed independent of the direction of movement of the plunger rod.

3. The syringe according to claim 1, further comprising a guide adapted to restrain a rotational movement of said plunger rod.

4. The syringe according to claim 1, wherein said predetermined play is at least a predetermined rotational play.

5. The syringe according to claim 1, wherein said plunger rod comprises at least one of a helical groove or a helical protrusion.

6. The syringe according to claim 5, wherein said first engagement member engages said at least one of a helical groove or said helical protrusion.

7. The syringe according to claim 1, wherein said engaging member is adapted to move in a plane generally perpendicular to a longitudinal direction of said plunger rod as the plunger rod is moved relative to the barrel.

8. The syringe according to claim 1, wherein the engaging member is tensioned at least in the second stage.

9. The syringe according to claim 1, wherein said engaging member comprises a protruding element adapted to engage said grooved surface.

10. The syringe according to claim 1, wherein said second engagement member is adapted to at least partly surround said plunger rod.

11. The syringe according to claim 1, wherein the gap is a gap in a thread fitting between the first engagement member and the plunger rod.

12. The syringe according to claim 1, wherein the gap is such that the predetermined relative movement is substantially the same in magnitude irrespective of the direction of movement of the plunger rod.

13. The syringe according to claim 1, further comprising:
a finger grip attached to the barrel,
wherein the second engagement member is disposed between the first engagement member and an interior of the finger grip in a circumferential direction.

14. The syringe according to claim 1, wherein the second engagement member is arranged circumferentially around the first engagement member, and the first engagement member is arranged circumferentially around the plunger rod.

15. The syringe according to claim 1, wherein the first cut-out is positioned so as to be offset from the second cut-out in a longitudinal direction of said plunger rod that is a direction of movement of the plunger rod relative to the barrel.

16. The syringe according to claim 3, wherein the first cut-out is positioned between the guide and the arm in a longitudinal direction of the plunger rod, and the arm is positioned between the first cut-out and the second cut-out in the longitudinal direction of the plunger rod.

* * * * *